United States Patent [19]

Feinstein

[11] 4,185,493

[45] Jan. 29, 1980

[54] VISCOSITY MEASURING INSTRUMENT

[76] Inventor: Robert A. Frosch, Administrator of the National Aeronautics and Space Administration, with respect to an invention of Samuel P. Feinstein, Sunland, Calif.

[21] Appl. No.: 918,535

[22] Filed: Jun. 23, 1978

[51] Int. Cl.² .................. G01N 11/06; G01N 11/08
[52] U.S. Cl. ................................. 73/56; 73/343 R; 264/40.4
[58] Field of Search ............... 73/56, 55, 343 R; 277/96.2, 103, 102, DIG. 6, 165, 212 F; 425/398, 376 R, 376 A; 264/40.4

[56] References Cited

U.S. PATENT DOCUMENTS

| | | | |
|---|---|---|---|
| 3,242,720 | 3/1966 | Zavasnik | 73/56 |
| 3,270,553 | 9/1966 | Ballman | 425/398 |
| 3,300,225 | 1/1967 | Shepler | 277/165 |
| 3,758,776 | 9/1973 | Frohne | 73/56 |
| 3,843,290 | 10/1974 | Sender | 73/343 R |

Primary Examiner—Stephen A. Kreitman
Assistant Examiner—Denis E. Corr
Attorney, Agent, or Firm—Monte F. Mott; John R. Manning; Paul F. McCaul

[57] ABSTRACT

A rheometer which is especially useful for measuring the viscosity of a heated coal-type material which undergoes phase changes at elevated temperatures, and which is of the type that includes a cylinder with a narrow exit and a piston for applying pressure to a sample in the cylinder to force the sample out through the exit. The piston includes a seal formed of a sheet of compressed carbon material which extends between the body of the piston and the walls of the cylinder, to form a substantially gas-tight fit that keeps in gases produced at elevated temperatures of a coal sample. The end walls of the cylinder and piston are tapered into a conical shape, and the sample is formed with conical surfaces to mate therewith, to provide a smooth outflow of material and high heat transfer to the sample from the cylinder and piston walls.

10 Claims, 4 Drawing Figures

VISCOSITY MEASURING INSTRUMENT

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

BACKGROUND OF THE INVENTION

High performance coal combusting and chemical conversion equipment can utilize a coal extruder that advances coal from a hopper to a pressurized combustion chamber, or the like and which forceably extrudes the coal into the chamber. During the extrusion process, the coal is rapidly heated from room temperature to several hundred degrees centigrade such as 500° centigrade. During such heating, the coal undergoes a great change in viscosity and bulk density, which is largely due to phase changes in the coal, including melting, vaporizing, polymerization and decomposition of certain coal components. The design of efficient coal extruders and other equipment that handles heated coal, can be greatly facilitated by knowledge about changes in the viscosity and bulk density of the particular coal which is to be used, as its temperature increases.

Typical prior art equipment for measuring viscosity includes a simple cylindrical chamber with a narrow opening at one end, and a simple piston which closely fits within the cylinder. The cylinder and piston could be heated to a high temperature such as 500° C., and an unheated solid coal sample could be inserted in the cylinder. The coal sample cannot be substantially preheated, since this would drive off the volatiles, oxidize the coal, and make it difficult to handle. The piston can then be pressed with great force into the cylinder, to extrude the coal which is rising in temperature, while measurements are made of the outflow of coal from the narrow opening. This technique has many deficiencies, including the fact that it is difficult to seal in volatiles in the coal, which therefore can escape past the piston to yield higher viscosity measurements than would be encountered in a coal extruder wherein the gases were trapped in the coal being extruded.

Another problem is that the temperature of the coal sample rises only slowly towards the temperature of the cylinder and piston, due to poor conductive heat transfer between the walls of the cylinder and piston and the coal sample. As a result, the large mass of the sample which lies between the end wall of the cylinder and the piston, will be at a much lower temperature than the sample portion being extruded through the small hole in the cylinder, so that the large portion of the sample will resist piston movement and prevent the application of most of the force applied to the piston to the portion of the sample which is being extruded through the hole. These and other great differences between the environment of the coal extruder utilized with a combustion chamber, and a sample utilized in a prior art rheometer, have made it difficult to obtain accurate measurements of coal viscosity to facilitate the design of efficient coal handling equipment. Accordingly, in the prior art, measurements have typically been on scales of relative viscosity such as the dial divisions per minute of the Geisler scale for a particular coal sample. A rheometer which enabled the measurement of the viscosity and/or bulk density of coal or other materials that underwent phase change at elevated temperatures, in a manner more closely similar to situations encountered in actual coal handling equipment, would facilitate the design of more efficient coal handling equipment.

SUMMARY OF THE INVENTION

In accordance with one embodiment of the present invention, a method and apparatus are provided for enabling the measurement of the viscosity of substances, especially those containing volatiles at elevated temperatures, with greater accuracy and at less cost than heretofore. The apparatus includes a cylinder with a narrow exit opening at one end and a piston which closely slides within the cylinder to apply force against a sample in the cylinder to force the sample out through the exit opening. In order to provide a relatively low cost and highly effective seal between the piston and cylinder, to keep in pressured gases, a seal is utilized which is formed of compressed graphite sheeting. A Grafoil sheet may be utilized which is constructed initially with a slightly greater diameter than the cylinder, and which self sizes itself to the cylinder walls to provide an extremely close fit therewith at low cost. In order to more rapidly heat a sample, the ends of the cylinder and piston are tapered and the sample is correspondingly tapered, to provide a large surface-to-volume ratio. A corresponding coal sample can be formed by compressing particles of coal under high pressure in a mold of appropriate shape.

The novel features of the invention are set forth with particularity in the appended claims. The invention will be best understood from the following description when read in conjunction with the accompanying drawings.

DESCRIPTION OF THE PREFERRED EMBODIMENT

Figure 1:
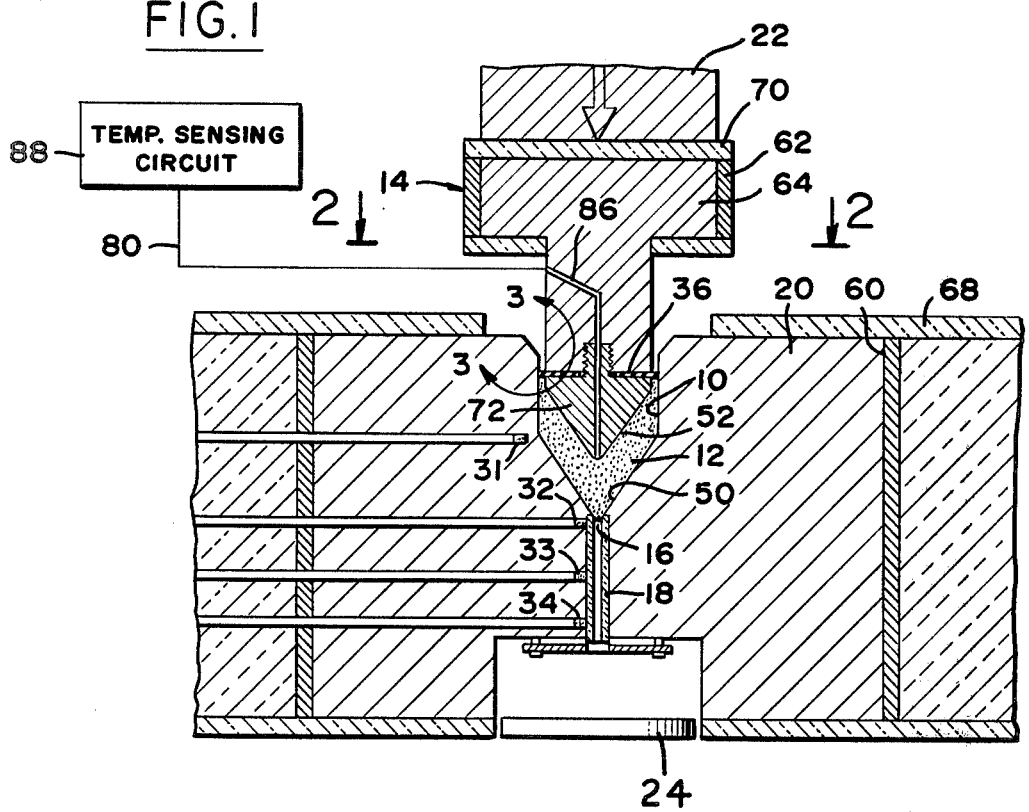
FIG. 1 is a sectional side view of a viscometer constructed in accordance with an embodiment of the invention.

FIG. 1 illustrates a capillary viscometer, which includes walls forming a chamber or cylinder 10 which is designed to receive a sample 12 of a material whose viscosity and/or bulk density are to be measured. A piston 14 is designed to be closely received in the cylinder 10 to apply large pressures to the sample, and an exit opening 16 in an end wall of the cylinder is designed to permit the outflow of the sample under the pressure. A capillary tube 18 is connected to the exit opening 16 to provide a long narrow path through which extruded material must pass, to provide a more accurate indication of the viscosity of the material. The apparatus is designed especially for use with a material which undergoes phase changes under the conditions of the test, and/or large variations in total bulk density, such as coal which releases volatiles when heated and which may undergo a change in bulk density from 1.0 to 1.4 grams per $cm^3$, and then down to 0.4 during a test. The apparatus can be used with coal or other coal-like, or coal-type, material which undergoes such phase changes or the like when heated to a temperature considerably above room temperature.

The viscometer can be utilized by first preheating a block 20 whose walls form the cylinder 10, and also by preheating the piston 14 to approximately the testing temperature such as about 500° C. for a coal sample. The sample 12 which has been preformed to match the shape of the cylinder and piston, is then inserted in the cylinder while the sample is in an unheated state, such as at room temperature. A coal sample cannot be appreciably preheated, since this would result in loss of volatiles. After the sample 12 has been inserted in the cylinder, the piston 14 is inserted and then pressed down by a force applying device 22 such as an Instron test machine, which can apply a large control force to the piston. The portion of the sample which flows down through the capillary tube 18 can be collected on a plate 24. Calculations based upon the initial weight, the volume outflow of the sample, force supplied to the piston, and the geometric dimensions of the apparatus, enable calculations of viscosity and bulk density throughout the test. A series of thermocouples 31-34 located adjacent to the sample in the cylinder 10 and the portion that flows along the capillary 18, permit the measurements to be related to the temperature of the sample.

One of the problems encountered in constructing equipment of the type shown in FIG. 1 to take measurements of a sample that decomposes to release volatiles during the test, is the sealing in of the volatiles. A test may last for a time such as 10 minutes, and it is important to keep in the volatiles, which would be retained in a typical coal extruding device utilized to advance coal into a chemical processing or combustion chamber. A fit between the piston seal and cylinder walls on the order of 100 microinches or less is required, especially where large pressures such as 3,000 psi are applied to the sample during the test.

Figure 3:
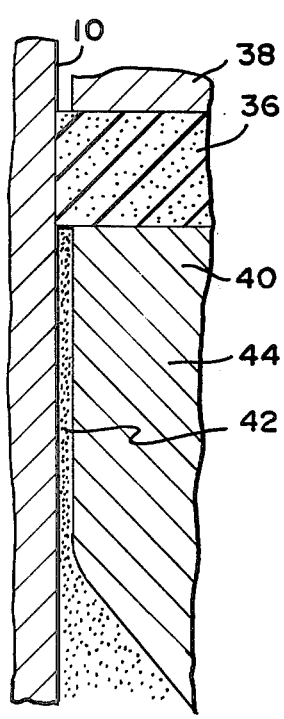
FIG. 3 is an enlarged view of the region 3—3 of FIG. 1.
Figure 2:
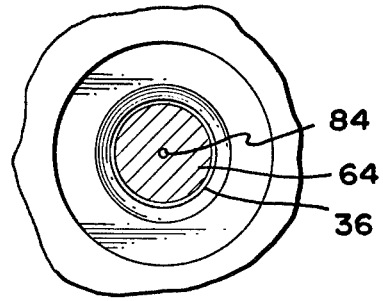
FIG. 2 is a view taken on the line 2—2 of FIG. 1.

In accordance with the present invention, a seal 36 is provided on the piston, which is formed of a compressed sheet of carbon material. Such a material manufactured by the Durametallic Corp. of Kalamazoo, Mich. and marketed under the name Grafoil, can be formed by pyrolyzing a sheet of felt, and then applying rolls to the sheet to compress it, to provide a compressed graphite sheet. It has been found that such a sheet can be utilized by cutting it to a size slightly larger than the diameter of the cylinder 10. The material self sizes itself to the correct diameter, and by slight bending and shearing off, forms an almost perfect seal against the walls of the cylinder 10. FIG. 3 shows one construction of the seal 36 which is utilized in a chamber 10 of a diameter of about three-quarters inch. The compressed carbon seal 36 had a thickness of 15 mils (thousanths of an inch) and, when sized to the cylinder, had a diameter about 3 mil greater than the diameter of adjacent portions 38, 40 of the piston. The cylinder had an 8 microinch finish. The compressed sheet carbon seal appears to bend as well as shear to provide a good seal. However, it also appears to be damaged by rapid reversal. Also, because of self sizing the seal must be replaced after each test. The low cost of the seal and the fact that replacement can be used to avoid cleaning, make this seal very practical.

The excellent sealing which has been obtained in the testing of heated coal, is believed to be due not only to the seal 36, but also to the formation of coke in a region 42 between a portion 44 of the piston and the walls 10 of the cylinder. The closeness of the walls of the piston and cylinder and the fact that both have been heated to a high temperature such as 500° C., can result in any coal lying in the space 42 being rapidly heated to the temperature of the adjacent walls. Such rapidly heated coal can turn partially into coke, which helps form a seal in the region 42 to aid in the sealing in of pressured gases. However, the compressed carbon seal 36 itself makes a good seal.

One of the problems encountered in making a test of a sample which must be greatly heated after insertion into the testing equipment, is the rapid heating of the sample. In order to accelerate such heating, the end wall 50 (FIG. 1) of the cylinder is concavely tapered into a conical shape, with the end of this cone leading into the exit opening 16. Similarly, the face 52 of the piston is convexly tapered into a substantially conical shape. WIth a sample 12 formed to a shape corresponding to the cylinder end wall and piston face, with one surface convex and the opposite surface concave, a large surface-to-volume ratio is obtained and with good contact between the sample and the cylinder and piston. The surfaces 50 and 52 of the cylinder and piston (and their side walls) have been preheated to a high temperature such as 500° C. when the relatively cold sample 12 is installed. The large areas afforded by the tapered surfaces 50, 52 result in the more rapid transfer of heat to the sample to more quickly heat it to the desired test temperature such as 400°-500° C. for testing coal. The tapered cylinder end wall 50 also has an advantage in that the coal undergoes a smaller change in direction when moving along the wall 50 into the exit opening 16, then would be encountered with an end wall that was perpendicular to the exit opening.

A typical prior art coal sample utilized in a rheometer, consisted of loose particles of a relatively coarse size such as particles of −8 mesh (up to one-tenth inch diameter). This resulted in poor heat transfer from the rheometer wall to the coal sample, and within the coal sample, since there was primarily point contact and large air spaces. In accordance with the present invention, a coal sample 12 was constructed by grinding a sample of a particular coal and screening it all to less than 80 mesh, and then pressing the coal particles under 12,000 psi into the shape shown in FIG. 1, with the sample having a diameter of about three-quarters inch. The small size of the particle and the pressed nature of the pellet, permitted good thermal conduction from the heated walls to the coal sample, and within the sample. The particles through the 80 mesh were sufficiently small to pass through a capillary 18 of 20 mil diameter. A series of tests were run, and it was found that the temperature along the capillary 18 was maintaine constant within $1\frac{1}{2}$° C.

It is estimated that it requires about 100 seconds to raise the temperature of the sample 12 which is originally at about room temperature, to the test conditions of about 450° C. The block 20 that forms the cylinder, and the piston 14, include band heaters 60, 62 that preheat them and maintain them at elevated temperature. The block 20 and cylinder 14 are both of large mass, so that there is minimal cooling of them by the cold sample. The block 20 and the body 64 of the piston were both constructed of molybdenum rather than stainless steel, because molybdenum has a higher heat conductivity than stainless steel, which allow the more effective transfer of heat to the sample. Insulation layer 68 was provided around the block 20, and insulator layers 70 were provided around the top portion of the piston.

After a test has been run, it is found that the capillary tubes should be disposed of and new ones used, since it is very difficult to clean out the coal therein. Similarly, it is found that the pressed carbon seal 36 is also damaged when moved out of the cylinder, and also must be replaced. The pressed carbon sheets seal 36 is of low cost, especially since it does not have to be machined to close tolerances to form an effective seal against the cylinder walls. The piston includes a brass block 72 that is screwed into the molybdenum portion 64. A separate brass block is utilized because brass is a good heat conductor and is of lower cost than the molybdenum material of the rest of the piston. It is found that if the brass block is not in good alignment with the sample, that it can be damaged, and therefore the relatively inexpensive brass block may be replaced instead of the more expensive molybdenum body.

In making viscometer measurements, it is preferable to utilize larger capillaries at low temperatures when the viscosity of the sample is high, and to utilize smaller capillary diameters when the temperature of the sample is high and its viscosity is low. The use of replaceable capillary tubes permits a series of tests to be run with capillary tubes of different diameters, with each capillary providing greatest accuracy for a certain temperature range of the coal sample. This is especially useful because it is found that the coal sample decreases in viscosity very quickly early in the test. This change is typically about 4 orders of magnitude during the test. Thus, after a test is made on a coal sample at a first temperature, another test is made on a similar sample but at a higher temperature and using a smaller inside diameter capillary tube if necessary.

Inasmuch as the coal sample is initially at a much lower temperature than the cylinder and piston, and it requires considerable time to heat the sample, knowledge of the actual coal sample temperature is very useful. The coal sample temperature can be measured by implanting a thermocouple temperature sensor 80 (FIG. 4) in the sample 12. The sensor 80 is positioned in the mold in which the sample is pressed to shape. The wires 82 leading from the thermocouple are then inserted through a narrow hole 84 formed in the brass block 72 of the piston through a hole 86 in the rest of the piston, and connected to a temperature sensing circuit 88 (FIG. 1) of a type well known for use with thermocouples. The portion of the wire 82 lying in the brass block 72 can be sealed to the block by a ceramic sealant.

Figure 4:
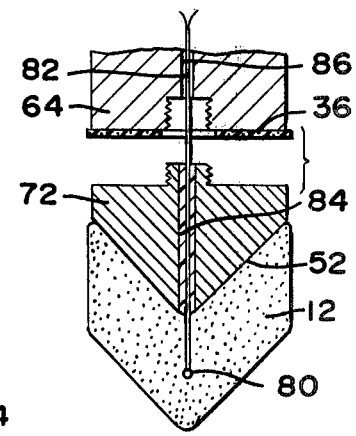
FIG. 4 is a partial sectional side view of the viscometer of FIG. 1, showing a manner in which it is utilized to prepare for the measuring of the characteristics of a sample.

When the molybdenum body 64 of the piston is being heated to the test temperature, the brass block 72 and coal sample can be kept separated from the body, as shown in FIG. 4. Then the brass block is threaded into the body 64, and the assembled piston is immediately inserted into the cylinder. The pressed carbon seal is a good heat conductor, so the brass block and sample can be heated in a moderate period of time.

The density of the coal sample can be measured as it is heated, by a method which includes replacing the capillary tube 18 with a solid rod to retain the sample whose temperature is rising. The force applying device 22 is utilized to apply a constant force to the piston, and movement of the piston is measured and recorded as a function of time and/or the temperature of the sample. Movement of the piston represents changes in the volume of the sample, and therefore changes in the density of the sample.

Thus, the invention provides apparatus for making accurate tests of the viscosity and bulk density of materials, especially those which undergo phase changes during the test, such as coal samples and other chemically reacting materials. A good seal is maintained between the piston and cylinder walls to keep in the volatiles, by the use of a seal formed of compressed carbon, which is of low cost and which is self sizing. Better heat transfer between preheated cylinder and piston walls and the sample is obtained by utilizing tapered surfaces at the end of the cylinder and piston, and by utilizing a preformed pellet of the sample material which is correspondingly formed to fit closely against the cylinder end wall and piston.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. Apparatus for measuring the viscosity of a material, comprising:

walls forming a sample holding cylinder with an exit opening; and a piston movable in said cylinder to compress a sample therein so it flows out through the exit opening;

said piston including a body of smaller diameter than the cylinder and a seal extending between said body and cylinder walls, said seal consisting of a sheet of compressed carbon.

2. The apparatus described in claim 1 including:

a sample of coal lying in said cylinder, said cylinder and piston walls being closely spaced in a region between said seal and said sample, and said cylinder and piston walls being at a temperature of a plurality of hundreds of degrees centigrade at said region, whereby to provide an additional seal below said carbon seal.

3. The apparatus described in claim 1 wherein: said sheet of compressed carbon has a thickness on the order of 15 mil and has a diameter greater than that of the adjacent piston portion on the order of 3 mil.

4. In a process for measuring characteristics of a material under elevated temperatures which includes placing a sample of the material in a cylinder and applying pressure to the sample with a piston, the improvement comprising:

reducing said sample to multiple particles;

heating said cylinder to a temperature higher than ambient temperature prior to installing said sample therein; and pressing said sample into a shape which mates with at least the walls of said cylinder prior to installing the sample into the cylinder, and then installing said sample into said cylinder, whereby to provide good heat conduction to the surface portion of the sample and from the surface portion to the deep interior portion of sample.

5. In a process for measuring characteristics of a material under elevated temperatures, which includes placing a sample of the material in a cylinder rod applying pressure to the sample with a piston, the improvement comprising:

implanting a temperature sensor in a quantity of separate particles of the material, so that the sensor is continuously surrounded by the material; and pressing the quantity of particles into a solid mass.

6. A method of measuring the viscosity of a coal-like material comprising:
   pressing the coal-like material into a pellet with a cylindrical outside surface and a convex face;
   inserting the pellet in a heated cylinder that has a concave end and an opening in the end; and
   inserting a piston into said cylinder and forcing the piston against the pellet therein.

7. A method for measuring the viscosity of a material, comprising:
   inserting a pellet of a material into a cylinder with an exit opening and a tube which is separate from the cylinder leading from said opening, wherein the walls of the cylinder have been heated to a temperature much higher than the pellet prior to the insertion, and the tube has a length which is a plurality of times greater than its wall thickness and a wall thickness less than half the wall thickness of the cylinder so that the tube is rapidly heated to the temperature of material flowing therethrough; and
   forcing a piston against said pellet while measuring the temperature of said tube and making measurments indicating the outflow of material from said cylinder through said tube.

8. A method for measuring changes in density of a coal-like material, comprising:
   installing a sample of the material in a cylinder which is closed except for a piston-receiving opening, and which has been preheated to a temperature higher than the sample;
   inserting a piston into the cylinder;
   applying a controlled force to the piston urging the piston against the sample, while permitting the piston to move; and
   measuring movements of the piston, whereby to enable a calculation of changes in sample density by the changes in sample volume indicated by piston movement.

9. In a process for measuring characteristics of a material under elevated temperatures, which includes placing a sample of the material in a cylinder and applying pressure to the sample with a piston, the improvement comprising:
   installing a temperature sensor which has at least one electrical wire extending therefrom, in a quantity of separate particles of the material;
   pressing the quantity of particles into a solid mass;
   installing said wire in a hole of a first portion of a piston, moving said sample against said first piston portion, and sealing said hole;
   installing said wire through a hole in a second piston portion; and
   heating the second portion of said piston while it is substantially thermally isolated from said first piston portion, moving said first and second piston portions together, and installing said sample and piston in the cylinder.

10. A method for measuring the viscosity of a coal-like material, comprising:
    inserting a pellet of a coal-like material into a cylinder with an exit opening and a tube leading from said opening, wherein the walls of the cylinder have been heated to a temperature much higher than the pellet;
    forcing a piston against said pellet while measuring the temperature of said tube and making measurements indicating the outflow of material from said cylinder through said tube; and
    heating said cylinder to a second predetermined temperature higher than said first named temperature, inserting a second pellet substantially identical to said first pellet, applying a piston, and measuring the temperature of a tube of smaller cross section connected to the exit opening and the outflow therefrom, whereby to obtain an indication of the temperature viscosity characteristics of the coal.

* * * * *